US012758158B2

(12) United States Patent
Dos Santos Da Fonseca

(10) Patent No.: US 12,758,158 B2
(45) Date of Patent: Oct. 13, 2026

(54) COMPUTER IMPLEMENTED METHOD FOR ADAPTIVE PHYSIOLOGY-BASED MONITORING OF A SUBJECT

(71) Applicant: KONINKLIJKE PHILIPS N.V., Eindhoven (NL)

(72) Inventor: Pedro Miguel Ferreira Dos Santos Da Fonseca, Borgerhout (BE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 349 days.

(21) Appl. No.: 18/541,142

(22) Filed: Dec. 15, 2023

(65) Prior Publication Data

US 2024/0206822 A1 Jun. 27, 2024

(30) Foreign Application Priority Data

Dec. 22, 2022 (EP) .................................... 22215859

(51) Int. Cl.
*A61B 5/00* (2006.01)
*A61B 5/0205* (2006.01)
*G16H 10/60* (2018.01)

(52) U.S. Cl.
CPC .......... *A61B 5/7267* (2013.01); *A61B 5/0205* (2013.01); *G16H 10/60* (2018.01)

(58) Field of Classification Search
CPC .......... A61B 2560/0252; A61B 5/0022; A61B 5/021; A61B 5/024; A61B 5/14532; A61B 5/4824; A61B 5/4848; A61B 5/7264; A61K 31/155; A61K 31/4045; A61K 31/4418; A61K 31/485; G06N 20/00; G16H 10/60; G16H 20/30; G16H 50/20; G16H 50/50; G16H 20/70; G16H 20/10
See application file for complete search history.

(56) References Cited

FOREIGN PATENT DOCUMENTS

| | | | | |
|---|---|---|---|---|
| WO | 2020070171 | A1 | 4/2020 | |
| WO | WO-2020221993 | A1 * | 11/2020 | ............ G16H 20/10 |

OTHER PUBLICATIONS

Devot et al., "Sleep/wake detection based on cardiorespiratory signals and actigraphy", 32nd Annual International Conference of the IEEE EMBS, Buenos Aires, Argentina, Aug. 31-Sep. 4, 2010, pp. 5089-5092.

(Continued)

*Primary Examiner* — Jon Eric C Morales
(74) *Attorney, Agent, or Firm* — Brynne J. Corcoran

(57) ABSTRACT

The invention provides a computer implemented method of providing physiological status monitoring. The method comprises receiving subject data (the subject data comprising physiological sensor data and reference physiological status data) and adapting a trained machine learning model for monitoring a physiological status. The trained machine learning model is configured to receive, as input, physiological sensor data and determine, as output, a physiological status of the subject. The trained machine learning model is configured to determine the output physiological status of the subject, based on the input physiological data, according to a plurality of weights. Adapting the trained machine learning model comprises re-training the trained machine learning model, based on the subject data by maintaining the values of a fixed set of the plurality of weights and changing the values of a variable set of the plurality of weights.

13 Claims, 9 Drawing Sheets

(56) References Cited

OTHER PUBLICATIONS

Long et al., "Sleep and Wake Classification with Actigraphy and Respiratory Effort Using Dynamic Warping", IEEE Journal of Biomedical and Health Informatics, vol. 18, No. 4, Jul. 2014, pp. 1272-1284.

Fonseca et al., "Sleep Stage Classification with ECG and Respiratory Effort." IOP Physiological Measurement 36: (2015) pp. 2027-2040.

Radha et al.. "Sleep stage classification from heart-rate variability using long short-term memory neural networks", Scientific Reports. 2019;9(1):14149, pp. 1-11.

Bakker et al., "Estimating sleep stages using cardiorespiratory signals: validation of a novel algorithm across a wide range of sleep-disordered breathing severity," Journal of Clinical Sleep Medicine, vol. 17, No. 7, pp. 1343-1354, Jul. 1, 2021.

Olsen et al., "Robust, ECG-based algorithm for Sleep Disordered Breathing detection in large population-based cohorts using an automatic, data-driven approach," Sleep Research Society, SleepJ, 2020, Vo. 43, No. 5, pp. 1-11.

Radha et al., "A deep transfer learning approach for wearable sleep stage classification with photoplethysmography," npj Digit. Med., vol. 4, No. 1, p. 135, Dec. 2021, pp. 1-11.

Papini et al., "Wearable monitoring of sleep-disordered breathing: estimation of the apnea-hypopnea index using wrist-worn reflective photoplethysmography", Scientific Reports, vol. 10, No. 1, p. 13512, Dec. 2020.

Karlen et al., "Adaptive Sleept Wake Discrimination for Wearable Devices", IEEE Transactions on Biomedical Engineering, IEEE, USA, vol. 58, No. 4, Apr. 1, 2011, pp. 920-926.

Van et al., "A Personalized Adaptive Algorithm for Sleep Quality Prediction using Physiological and Environmental Sensing Data", 2021 8th Nafosted Conference on Information and Computer Science (NICS), IEEE, Dec. 21, 2021, pp. 113-119.

Radha et al., "LSTM Knowledge Transfer for HRV-based sleep staging" Arxiv.org. Cornell University Library, 201 Olin Library Cornell University Ithaca, NY, Sep. 2018, pp. 1-11.

Phan et al., "Personalized Automatic Sleep Staging with Single-Night Data: a pilot study with Kullback-Liebler divergence regularization", Physiological Measurement, vol. 14, Jun. 30, 2020, pp. 64004.

* cited by examiner

COMPUTER IMPLEMENTED METHOD FOR ADAPTIVE PHYSIOLOGY-BASED MONITORING OF A SUBJECT

CROSS REFERENCE TO RELATED APPLICATION

This application claims the benefit of European Patent Application No. 22215859.4, filed Dec. 22, 2022. This application is incorporated by reference herein.

FIELD OF THE INVENTION

The present invention relates to a computer implemented method for personalized physiology-based monitoring of a subject. In particular, the present invention relates to a computer implemented method for monitoring the subject's physiological status, wherein the method is personalized to the subject.

BACKGROUND OF THE INVENTION

In the field of physiological status monitoring, physiological parameters are measured and analyzed to assess the physiological status of a subject. Trained machine learning models can be used to determine physiological status, based on input physiological parameter data. In general, the training data for trained machine learning models includes data from a large number of participants. The participants may vary in multiple ways including age, drug/medication intake and health (e.g., the presence of cardiac, respiratory or other sleep comorbidities).

One type of physiological status monitoring is sleep monitoring. In polysomnographic (PSG) sleep studies, sleep stages are ordinarily measured using sensors for measuring neurological parameters—for example, electroencephalogram (EEG) sensors, electrooculography (EOG) sensors and/or electromyograph (EMG) sensors. However, the use of these sensors can disrupt the subject's sleep. Additionally, in order to work effectively the sensors must be applied with care, usually requiring the help of an expert.

The neurological sensor data can be evaluated manually, to identify sleep stages and sleep events. However, this is a time-consuming task that requires the manual effort of a trained sleep technician. Automatic scoring algorithms alleviate the need for human input and allow for new clinical applications such as real-time interventions during sleep, or remote monitoring (for example at home during therapy or for follow-up).

In general, it is possible to monitor some physiological conditions (i.e., physiological states, such as sleep) using sensors for measuring autonomic nervous system activity (e.g., cardiorespiratory activity). Cardiorespiratory information can be measured by unobtrusive methods such as wrist-worn PPG sensors, ballistocardiographic bed sensors, seismocardiographic accelerometers mounted on or in the vicinity of the patient's chest, etc. Because sensors for obtaining cardiorespiratory information are unobtrusive, these sensors have the important advantage that they can be used by the subject, at home, for prolonged periods of time (e.g., during a Home Sleep Test). By contrast, PSG sleep studies are typically conducted over one night, or two nights (at most).

Home sleep tests (HSTs) involve reduced polygraphic setups (excluding or using a reduced set of neurological sensors e.g., sensors for measuring EEG, EOG, EMG), in which at least the following parameters are measured: airflow, SpO2 and respiratory effort. Although these setups are simpler than those required for a full PSG sleep study, they are still not suitable for long-term monitoring at home. Because HSTs involve monitoring at least airflow, SpO2 and respiratory effort, the data obtained from a HST can be used to perform traditional scoring of SBD events (according to e.g., the AASM guidelines)—either manually, or automatically. If fewer and/or different parameters are measured, it is no longer possible to perform traditional scoring of SBD events.

Some HSTs involve the use of cardiorespiratory data to monitor sleep. Cardiorespiratory-based sleep stage classification has been increasingly studied in recent years, including classification of sleep stages using heart-rate variability (HRV) and respiratory variability parameters. These parameters can be measured using cardiorespiratory sensors such as those mentioned above.

For example, PSG studies involve calculating sleep-related measures (e.g., measures indicative of the presence and severity of Obstructive Sleep Apnea) which are determined based partly on total sleep time. Total sleep time is not necessarily determined in an HST. While total sleep time can be substituted for total recording time, this approach leads to less accurate measurements. Some HSTs involve the use of cardiorespiratory data to estimate total sleep time, to obtain more accurate measurements.

Recent developments have avoided the explicit design and computation of HRV parameters for monitoring sleep and instead use deep neural networks comprising layers dedicated to feature extraction. Some results have been achieved for automatic sleep staging based on lower-level input signals such as instantaneous heart rate signals, or raw respiratory effort signals. Some other approaches have focused not on detecting sleep stages, but on the detection of other important events in sleep, such as sleep disordered breathing (SDB) events like obstructive or central apneas and hypopneas, arousals, etc. These are traditionally scored during a PSG sleep study, or alternatively, based on HSTs.

Accordingly, surrogate parameters can be used to score SBD events in a "non-traditional" manner; for example, it has been recently shown that a deep learning neural network could also be used to detect disordered breathing events using electrocardiography (ECG) sensors (M. Olsen, E. Mignot, P. J. Jennum, and H. B. D. Sorensen, "Robust, ECG-based algorithm for Sleep Disordered Breathing detection in large population-based cohorts using an automatic, data-driven approach," Sleep, p. 276, November 2019).

Other types of physiological status monitoring, which may rely on detecting the autonomic expression of a physiological status, include fitness monitoring and health condition monitoring (e.g., cardiac conditions, such as atrial fibrillation, blood pressure).

In any model that relies on autonomic expression of a physiological status there can be significant differences between subjects depending on a variety of factors, for example age, intake of drugs and medication, and/or the presence of cardiac, respiratory or other sleep comorbidities.

Some sleep studies involve monitoring a reduced set of parameters compared to a typical PSG. For example, HSTs may involve the monitoring of neurological activity, but with fewer sensors than would typically be used in a PSG. Rather than placing a large number of EEG electrodes over the subject's head, the HST can make use of just one or two electrodes. However, these set-ups may suffer from subject-dependent variations such as different impedance between the frontal electrodes and the skin (some subjects sweat more than others) different amount of motion artifacts (some subjects may move more than others).

Article "Personalized automatic sleep staging with single-night data: a pilot study with Kullback-Leibler divergence regularization" by Huy Phan et. al, published in Physiological Measurement vol 41, on Jun. 30, 2020, discloses a method for automatic sleep staging for longitudinal sleep monitoring via personalization of algorithms based on individual characteristics extracted from sleep data recorded during the first night.

It would be desirable to provide an improved way of monitoring the physiological status of a subject. In particular, it would be desirable to provide an improved way of identifying sleep stages and/or sleep events.

SUMMARY OF THE INVENTION

The invention is defined by the claims.

According to examples in accordance with an aspect of the invention, there is provided a computer implemented method of providing physiological status monitoring, the method comprising: receiving subject data comprising physiological sensor data; and adapting a trained machine learning model for monitoring a physiological status. The trained machine learning model is configured to determine the physiological status of the subject based on the physiological sensor data. The trained machine learning model has a plurality of fixed weights and a plurality of variable weights. Adapting the trained machine learning model comprises: generating a first re-trained machine learning model by adapting the trained machine learning model by maintaining the values of the plurality of fixed weights, and changing values of a first number of the plurality of variable weights; determining a level of agreement between the trained machine learning model and the first re-trained machine learning model; in response to the level of agreement, generating a second re-trained machine learning model by adapting the trained machine learning model by maintaining the values of the plurality of fixed weights, and changing values of a second number of the plurality of variable weights. The second number is different from the first number.

The trained machine learning model is configured to determine an output according to learned parameters (weights) determined in the process of training the machine learning model. The trained machine learning model is re-trained using data personalized to the subject, i.e., the physiological sensor data. In this way it is possible to achieve improved (more accurate) monitoring of the physiological status. In particular, re-training the trained machine learning model using a re-training procedure in which only some of the machine learning model's weights are changed to adjust to the subject's characteristics (i.e. the other weights being fixed) the method can adjust the trained machine learning model enough to personalize the machine learning model to the subject without training the machine learning model to be overly specific to the characteristics of the time period(s) over which the subject data was obtained. Re-training the machine learning model in this way makes it possible to personalize the machine learning model to the subject in a convenient way (e.g., only a single night or a few nights of physiological sensor data is needed for the re-training process).

By determining the level of agreement between the trained machine learning model and the first re-trained machine learning model, it can be determined how much the first re-trained machine learning model is different from the trained machine learning model. There is likely some difference, because the first re-trained machine learning model takes the physiological sensor data into account. The physiological sensor data is personal to the subject and was not available when the trained machine learning model was trained. When the level of agreement indicates a small difference, the trained machine learning model uses the changed first number of variable weights to provide physiological status monitoring. The generation of the second re-trained machine learning model may be omitted in this case. Alternatively, the second re-trained machine learning model may be generated, using the second number of the plurality of variable weights. The second number is larger than the first number. Because the second number is larger than the first number, it is expected that the second re-trained machine learning model differs more from the trained machine learning model than the first re-trained machine learning model. Because of this difference, the second re-trained machine learning model may be more accurate than the first-retrained machine learning model, as the second re-trained machine learning model is more affected by the physiological sensor data.

However, the difference between the first re-trained machine learning model and the trained machine learning model should not be too large, because this would indicate overfitting of the machine learning model. When overfitting, there is a large change in the variable weights. This large change reduces the accuracy of the first re-trained machine learning model, even though the first re-trained machine learning model matches the specific session in which the physiological sensor data were obtained very well. When the level of agreement indicates a large difference between the trained machine learning model and the first re-trained machine learning model, the second re-trained machine learning model is generated based on the second number of variable weights. The second number is smaller than the first number, to reduce the effect of the physiological sensor data on the second re-trained machine learning model.

By re-training the trained machine learning model based on different numbers of variable weights, a more accurate re-training can be obtained compared to changing the values of the same number of variable weights for each re-training. Known optimization methods may be used to determine the first number and the second number of variable weights to re-train the trained machine learning model.

In an embodiment, the level of agreement is indicative of a difference between the values of the first number of the plurality of variable weights of the trained machine learning model, and the values of the first number of the first re-trained machine learning model. For example, in case the values of the first number differ only slightly between the trained machine learning model and the first re-trained machine learning model, the level of agreement is high, which indicates that there is only a small difference. In case the values of the first number differ substantially between the trained machine learning model and the first re-trained machine learning model, the level of agreement is low, which indicates that there is a big difference. For example, a threshold is provided for the level of agreement. In case the level of agreement exceeds the threshold, the difference is too large. This may, for example, be indicative of overfitting. Then, the second re-trained machine learning model is generated based on the second number of variable weights. The second number may be smaller than the first number to limit the effect of the physiological sensor data on the trained machine learning model. The second number may be larger than the first number, to allow the second re-trained machine learning model to take into account the physiological sensor data, while only making small changes to each of the second number of variable weights.

In an embodiment, the level of agreement is indicative of a difference of a performance of the trained machine learning model and a performance of the first re-trained machine learning model. In this embodiment, the output of the trained machine learning model and the output of the first re-trained machine learning model are compared. The outputs relate to the physiological status monitoring. The performance indicates how well the physiological status monitoring is performed. In case the performance of the first re-trained machine learning model is worse than that of the trained machine learning model, the second re-trained machine learning model is generated. Then the performance of the second re-trained machine learning model is compared with the performance of the trained machine learning model and/or of the first re-trained machine learning model. The second number of variable weights may be larger or smaller than the first number of variable weights in an attempt to improve the performance of the second re-trained machine learning model compared to the first re-trained machine learning model.

The trained machine learning may be a trained neural network.

The trained neural network may be re-trained using transfer learning. By adapting the trained neutral network based on data personalized to the subject, it is possible to use the re-trained neural network to achieve improved (more accurate) monitoring of the physiological status.

The physiological sensor data may indicate a physiological parameter indicative of a physiological status, and the subject data may comprise reference physiological status data indicating the physiological status correlated with the physiological parameter.

The physiological parameter may be a parameter related to the autonomic nervous system. For example, the parameter may indicate heart rate and/or heart rate/pulse variability and/or may indicate respiratory information. The physiological status may be a sleep stage, a condition (e.g., sleep disordered breathing, such as obstructive apnea, central apnea or hypopnea) or a sleep/arousal event. Alternatively, the physiological status may not be related to sleep. The physiological sensor data may be indicative of physical fitness. In some examples, the physiological status may indicate a condition such as a cardiac disorder (e.g., atrial fibrillation) or may indicate blood pressure.

The trained machine learning model may be configured to provide sleep monitoring, the physiological sensor data comprises autonomic nervous system activity data, and the physiological status is a sleep stage, a sleep disordered breathing event or an arousal event.

The physiological sensor data may comprise accelerometer data, cardiac data and/or respiratory data.

The cardiac data may comprise data indicative of the subject's heartbeat pattern (e.g. data indicative of interbeat interval). For example, the cardiac data may comprise heart rate variability data.

The physiological sensor data may comprise neurological activity data and/or central nervous system activity data.

The physiological sensor data may comprise cardiac data and the physiological status is a cardiac-related condition.

The cardiac data may comprise data indicative of the subject's heartbeat pattern (e.g. data indicative of interbeat interval). For example, the cardiac data may comprise heart rate variability data.

The method may further comprise obtaining subject data by:

obtaining, over a re-training period, representative physiological sensor data, wherein the representative physiological sensor data comprises autonomic nervous system activity data;

obtaining reference physiological status data, wherein the reference physiological status data indicates a ground truth associated with the monitored physiological status during the re-training period.

The reference physiological condition data can be obtained using the types of sensors used in PSG sleep studies (e.g., ECG, EOG, EMG sensors), as opposed to sensors for measuring autonomic nervous system activity.

The method may further comprise generating the trained machine learning model by:

obtaining physiological sensor training data for a plurality of participants;

obtaining reference training information, wherein the reference training information indicates a ground-truth associated with monitored physiological status;

inputting the physiological sensor training data and the reference training information into to the machine learning model.

The method may further comprise:

obtaining a plurality of subject data sets, each data set corresponding to a respective time period; and determining the number of fixed weights based on the number of subject data sets.

The method may comprise obtaining a plurality of subject data sets, each data set corresponding to a respective time period, the method further comprising:

generating the first re-trained machine learning model by adapting the trained machine learning model based on a first subject data set corresponding to a first time period;

generating the second re-trained machine learning model by adapting the trained machine learning model based on the first subject data set and a second subject data set, the second subject data set corresponding to a second time period; and evaluating the performance of the first re-trained machine learning model and the second re-trained machine learning model; and in response to determining that the performance of the first re-trained neural network is superior to the second re-trained machine learning model, preventing re-training of the machine learning model from using the second subject data set.

The second data set may comprise older data than the first data set.

Evaluating the performance of the first trained machine learning model and the second trained machine learning model may comprise:

for each of the first re-trained machine learning model and the second re-trained machine learning model, determining the level of agreement between the output of the trained machine learning model and the adapted machine learning model.

In accordance with another aspect of the invention, there is provided a system for monitoring a physiological status, the system comprising:

a processor configured to carry out the above-described method.

The system may further comprise a database storing the trained machine learning model and the subject data. The processor is configured to retrieve the trained machine learning model and the subject data from the database and/or to retrieve from a physiological sensor the physiological sensor data. Optionally, the physiological sensor is configured to measure an autonomic nervous system parameter.

In accordance with another aspect of the invention, there is provided a computer program product comprising computer program code means which, when executed on a computing device having a processor, cause the processor to perform all of the steps of the above-described method.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
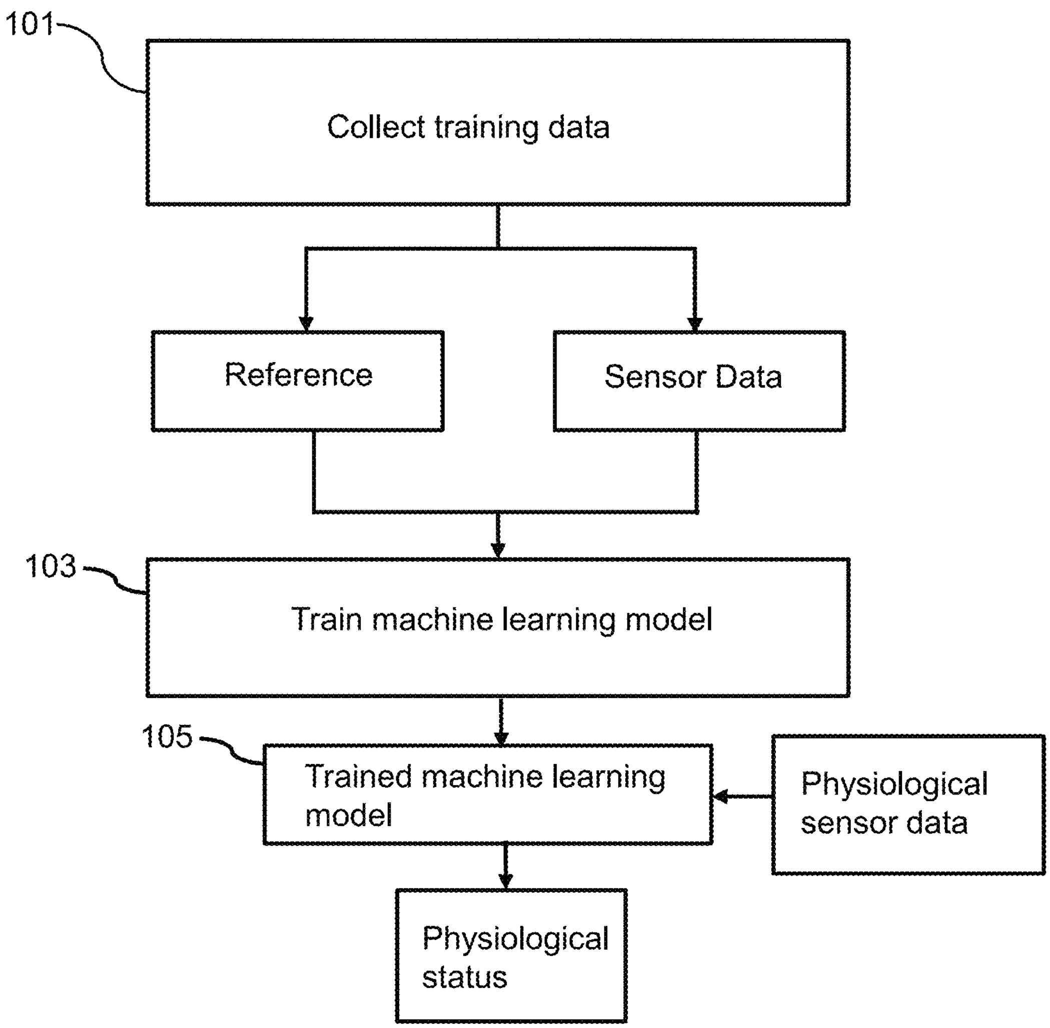
FIG. 1 shows a flow diagram illustrating an example training process for generating a trained machine learning model.

The invention will be described with reference to the Figs.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figs are merely schematic and are not drawn to scale. It should also be understood that the same reference numerals are used throughout the Figs to indicate the same or similar parts.

The invention provides a computer implemented method of providing physiological status monitoring. The method comprises receiving subject data (the subject data comprising physiological sensor data and optionally reference physiological status data) and adapting a trained machine learning model for monitoring a physiological status using the subject data. The trained machine learning model is configured to receive, as input, physiological sensor data and determine, as output, a physiological status of the subject. The trained machine learning model is configured to determine the physiological status of the subject, based on the input physiological sensor data, according to a plurality of weights. The trained machine learning model has a plurality of fixed weights and a plurality of variable weights. Adapting the trained machine learning model comprises: generating a first re-trained machine learning model by adapting the trained machine learning model by maintaining values of the plurality of fixed weights, and changing values of a first number of the plurality of variable weights; determining a level of agreement between the trained machine learning model and the first re-trained machine learning model; and in response to the level of agreement, generating a second re-trained machine learning model by adapting the trained machine learning model by maintaining the values of the plurality of fixed weights, and changing values of a second number of the plurality of variable weights. The second number is different from the first number.

FIG. 1 shows a flow diagram illustrating an example initial training process for generating a trained machine learning model.

The trained machine learning model 105 is a self-trained algorithm that processes input data in order to produce or predict output data. Here, the input data comprises subject physiological sensor data and the output data comprises a physiological status of the subject.

Suitable machine-learning algorithms for being employed in the present invention will be apparent to the skilled person. Examples of suitable machine-learning algorithms include decision tree algorithms and artificial neural networks. Other machine-learning algorithms such as logistic regression, support vector machines or Naïve Bayesian models are suitable alternatives.

The structure of an artificial neural network (or, simply, neural network) is inspired by the human brain. Neural networks are comprised of layers, each layer comprising a plurality of neurons. Each neuron comprises a mathematical operation. In particular, each neuron may comprise a different weighted combination of a single type of transformation (e.g., the same type of transformation, sigmoid etc. but with different weightings). In the process of processing input data, the mathematical operation of each neuron is performed on the input data to produce a numerical output, and the outputs of each layer in the neural network are fed into the next layer sequentially. The final layer provides the output.

Methods of training a machine-learning algorithm are well known. Typically, such methods comprise obtaining a training dataset, comprising training input data entries and corresponding training output data entries. An initialized machine-learning algorithm is applied to each input data entry to generate predicted output data entries. An error between the predicted output data entries and corresponding training output data entries is used to modify the machine-learning algorithm. This process can be repeated until the error converges, and the predicted output data entries are sufficiently similar (e.g., ±1%) to the training output data entries. This is commonly known as a supervised learning technique.

For example, where the machine-learning algorithm is formed from a neural network, (weightings of) the mathematical operation of each neuron may be modified until the error converges. Known methods of modifying a neural network include gradient descent, backpropagation algorithms and so on.

The training input data entries correspond to example physiological sensor data. The training output data entries correspond to physiological statuses.

The training input data comprises physiological sensor data obtained in respect of a representative population of subjects (rather than data specific to the subject for which physiological status monitoring is to be provided via the trained machine learning model).

In the example training process illustrated in FIG. 1, training data is collected, 101, from a representative population (for example, in a clinical setting such as a hospital). The training data is representative of the type of data that will be measured when the trained computer model is employed by the end-user. The training data is obtained using a similar physiological sensor or the same type of physiological sensor. The physiological sensor used to obtain the training data and the physiological sensor used by the end-user measure the same parameter(s). For example, if the physiological parameter to be measured is heart rate variability, the training data may be collected using an ECG sensor while the physiological sensor used by the end-user may be a PPG sensor. The training data comprises physiological sensor data and reference data, wherein the reference ("ground truth") data indicates true physiological status. The physiological sensor data is obtained by using a physiological sensor (or an array of physiological sensors) to monitor a physiological parameter or a plurality of physiological parameters. The machine learning model is trained, 103, based on the training data to produce, 105, a trained machine learning model for monitoring the physiological status of the subject based on physiological sensor data obtained for the subject (i.e., using a sensor for measuring the same parameter(s) monitored for the training data).

In an example, the training process illustrated in FIG. 1 is used to generate a trained machine learning model for providing sleep monitoring. In this example, it is envisaged that the trained machine learning model will use end-user cardiac data (e.g., instantaneous heart rate data calculated from inter-beat intervals detected from e.g. a PPG sensor) and body movement data measured by an accelerometer. Accordingly, training data comprising cardiac data and body movement data is obtained for a representative population. The training data also includes reference data collected using electroencephalogram (EEG), electrooculography (EOG) and/or electromyograph (EMG) sensors. The reference data is manually, or automatically, scored to identify sleep stages and/or sleep disordered breathing events. The machine learning model can therefore be trained to identify sleep stages and/or sleep disordered breathing events based on cardiac data and body movement data.

Figure 2:
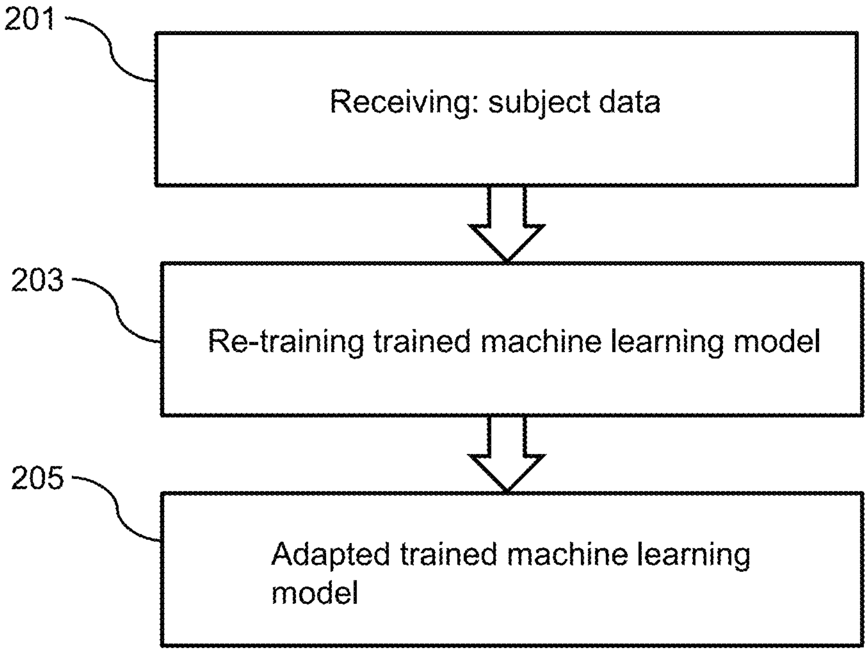
FIG. 2 shows a flow diagram illustrating an embodiment of a computer implemented method of providing physiological status monitoring of a subject.

FIG. 2 shows a flow diagram illustrating an embodiment of a computer implemented method of providing physiological status monitoring of a subject. The method comprises adapting a trained machine learning model based on subject data, wherein the trained machine learning model is configured to determine a physiological status of the subject based on physiological sensor data.

The method comprises receiving, 201, subject data. The subject data comprises physiological sensor data, obtained from a physiological sensor for measuring a parameter indicative of a physiological status of the subject. The subject data may also include reference physiological status data, which indicates a physiological status correlated with the physiological sensor data. For example, the physiological sensor data may comprise cardiac data and body movement data and the reference physiological status data may indicate the sleep stage of the subject (wherein the trained machine-learning algorithm was trained e.g., according to the process illustrated in FIG. 1 based on cardiac data and body movement data obtained from a representative population). The subject data is used to adapt the trained machine learning model, thereby personalizing the trained machine learning model to the subject. The method comprises re-training, 203, the trained machine learning model based on the subject data.

The re-training procedure is carried out by varying the values of some of the weights defining the trained machine learning model, whilst maintaining the values of other weights. The weights that can be varied form a set of variable weights. The weights that are fixed form a set of fixed weights. For example, the set of variable weights contains fewer weights than the set of fixed weights. The values of the variable weights are changed to optimize the accuracy of the machine learning model in outputting physiological status based on the input physiological sensor data.

In general, the process for determining which weights should form the set of variable weights is an iterative process, such as a gradient descent process (which relies on assessing the steepest or stochastic gradient descent over a loss function) or an evolutionary algorithm. For example, known backpropagation training techniques for training neural networks can be used.

In some embodiments, the weights are assigned to the set of fixed weights or the set of variable weights during development of the trained machine learning model (i.e., during the process described in connection with FIG. 1). Accordingly, in these embodiments, the division of weights between the set of fixed weights and the set of variable weights is pre-determined. The process for determining which weights are fixed and which weights are variable involves iteratively searching for the combination of fixed/variable weights that leads to the best performance. This is only carried out, during the design and development of the trained machine learning model (not during the re-training process).

In some other embodiments, the process for selecting fixed weights and variable weights is carried out as part of the re-training of the machine learning model. For example, the selection process can be carried out by iteratively choosing a set of variable weights, varying the values of the variable weights (e.g., using a backpropagation training technique) and evaluating the performance of the machine learning model using the new values for the variable weights. By iteratively repeating this procedure, it is possible to optimize the selection of and values for the variable weights.

The first number of the plurality of variable weights, and the second number of the plurality of variable weights are subsets of the set of variable weights. The first number is at least 1. The second number is at least 1.

By re-training the trained machine learning model in this way, the method generates, 205, an adapted trained machine learning model that is personalized to the subject.

In general, the subject data may be collected over a single data collection period or over multiple data collection periods. The data collection period may be few hours or may cover a longer period such as a full day/night. The data collection may be collected over multiple days and/or nights. For example, where the monitored physiological status is sleep-related, the subject data may be collected over a single night or multiple nights.

If the subject data is collected over a relatively short period (e.g., a single night), the re-training process may limit the number of layers of the trained machine learning model for which the respective weight value is changed. Where the subject data is collected over a relatively long period (e.g., multiple nights), more layers can be involved in the re-training process. That is, the weights of multiple layers can be varied, and more variable weights may be varied for a process involving a longer data collection period as compared to the number of variable weights varied for a shorter data collection period.

Where the subject data comprises multiple sets of data, corresponding to different data collection time periods, the method may further comprise assessing the subject data to determine which data sets to include in the re-training process. For example, if the training data collection periods are not consecutive, but instead, separated by longer periods of time (e.g., years), the method may comprise iteratively determining whether older data should be used in the adaptation step or not. This can be achieved by assessing the performance of the model when it uses all available data to perform the adaptation in comparison to the reference physiological status data. If performance is (substantially) inferior when the model is re-trained using subject data that includes older data sets, the subject data used for re-training may be restricted to more recent data sets.

Adapting the trained machine learning model comprises generating a first re-trained machine learning model by adapting the trained machine learning model by maintaining values of the plurality of fixed weights, and changing values of a first number of the plurality of variable weights. Adapting the trained machine learning model comprises determining a level of agreement between the trained machine learning model and the first re-trained machine learning model. Adapting the trained machine learning model comprises, in response to the level of agreement, generating a second re-trained machine learning model by adapting the trained machine learning model by maintaining the values of the plurality of fixed weights, and changing values of a second number of the plurality of variable weights. The second number is different from the first number.

For example, the level of agreement is indicative of a difference between the values of the first number of the plurality of variable weights of the trained machine learning model and the values of the first number of the first re-trained machine learning model.

For example, the level of agreement is indicative of a difference of a performance of the trained machine learning model and a performance of the first re-trained machine learning model.

For example, the method may comprise generating the first re-trained machine learning model by adapting the trained machine learning model based on a first subject data set corresponding to a relatively old data collection period and generating the second re-trained machine learning model by adapting the trained machine learning model based on both the first subject data set and a second subject data set, wherein the second subject data set was collected relatively recently. The performance of the first re-trained machine learning model and the second re-trained machine learning model is evaluated and if the performance of the second re-trained machine learning model is superior only the first re-trained model is output as the retained machine learning model for use by the subject in physiological status monitoring.

Selecting training data in this way can help to reduce expected physiological changes associated with advancing age, or the development of additional conditions. In this way, the model reflects the most recent condition and characteristics of an individual.

As discussed above, if the subject's characteristics change significantly over time, the machine learning model may need to be re-trained again. The method may comprise automatically detecting a deterioration in performance, to assess whether further re-training is appropriate. This can be achieved by generating the first re-trained machine learning model after a certain time interval has passed, for example several days, or weeks, or months. The level of agreement between the trained machine learning model and the first re-trained machine learning model is measured as a baseline, e.g. by means of epoch-per-epoch accuracy or Cohen's kappa coefficient of agreement (or any other measure for assessing agreement), e.g., with the first night(s) available after the adaptation/re-training night). The determined level of agreement reflects how much the trained machine learning model (i.e., the machine learning model trained on representative training data only) model differs from the first re-trained machine learning model (i.e., the machine learning model as re-trained using subject data). In regular (e.g., night-to-night) use, this comparison can be performed continuously. If the level of agreement starts decreasing substantially, and consistently for a period of time, this may mean that the characteristics of the subject have changed substantially since the last time the machine learning model was re-trained. In response to determining that the level of agreement has decreased, the method may comprise outputting a warning indicating deterioration in performance. In response, the method may comprise reverting to the original trained machine learning model and/or generating an output indicating that that a new adaption session is required to the update the machine learning model.

An update of the model (by re-training) may also be triggered by receipt of a signal indicating that subject circumstances have changed. For example, detected changes in an accompanying system (e.g., patient medical record, which indicates the new diagnosis of a comorbid condition, or changed medication known to impact the surrogate measures that the algorithm is based on, etc.) may cause a signal indicating that subject circumstances have changed to be issued.

In some embodiments, the physiological sensor data comprises data obtained from a physiological sensor that was also used during a study (e.g., a PSG sleep study) to train the machine learning model. For example, the physiological sensor data may include data obtained from a wearable/nearable physiological sensor. As an example of a wearable physiological sensors, typical sleep tracking devices comprise wearable physiological sensors (e.g., wrist-worn PPG and accelerometer). The same type of sensor used to obtain the training data (e.g., at the same time as a PSG study in the clinic) is used to obtain the physiological sensor data for re-training the machine learning model. This is particularly useful for providing long-term sleep monitoring application (weeks, months or even longer).

In some embodiments, the physiological sensor data is data obtained from a neurological sensor. For example, the trained machine learning model may be used with a sensor array for carrying out an HST using a reduced set of EEG sensors. The physiological sensor data may therefore comprise EEG sensor, and the machine learning model may be re-trained using EEG data.

Figure 3:
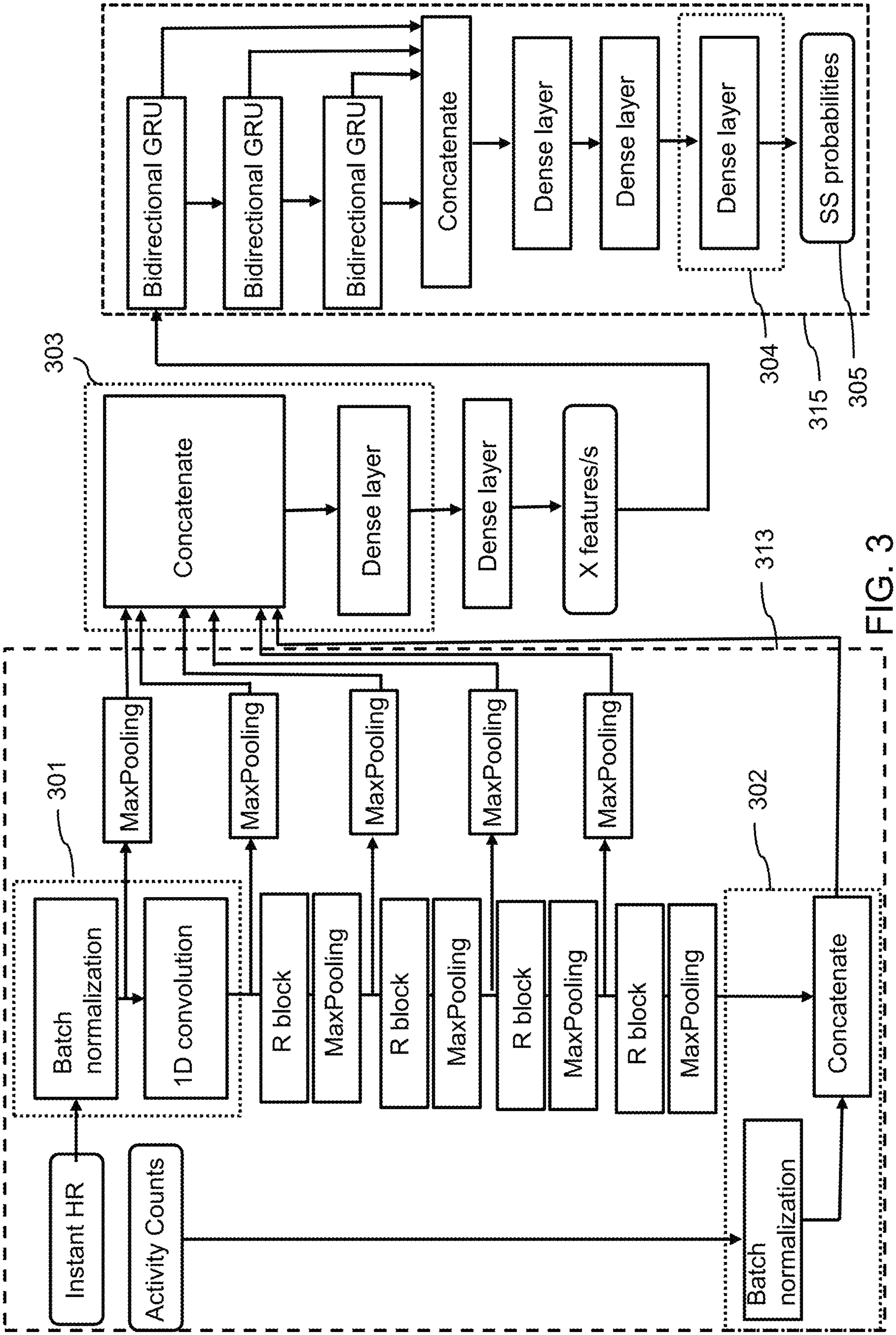
FIG. 3 shows a flow diagram illustrating the architecture of a machine learning model according to one or more embodiments of the invention.

FIG. 3 shows a flow diagram illustrating example embodiment of the computer implemented method of providing physiological status monitoring of a subject. In this embodiment, the machine learning model is a neural network for monitoring the sleep status of a subject. The subject data, including cardiac data (instant HR) and body movement data (activity counts), is obtained from a PPG sensor and accelerometer respectively. The neural network comprises multiple operational layers, including the first layer 301, the second layer 302, the third layer 303 and the fourth layer 304, and an output layer 305. Each layer comprises a plurality of neurons, which carries out a mathematical operation. Each neuron in the layer comprises a different weighted combination of a particular type of transformation.

The neural network comprises a feature extraction block 313 for extracting features based on the input physiological sensor data. Feature extraction is carried out to reduce the temporal resolution of the input physiological sensor data to match the desired output (the input instant HR is sampled at 10 Hz while the output sleep stages have a resolution of 1 value—one sleep stage—per 30 seconds). Additionally, feature extraction can increase the richness and complexity of the features. During training the network "learns" adequate feature representations that optimally map the input data (Instant HR and Activity Counts) to the output sleep stages.

a real-time sleep staging system, this could be changed to rely on unidirectional RNNs instead.

As illustrated in FIG. 3, the machine learning model output sleep stage probabilities, based on the subject data.

Figure 4:
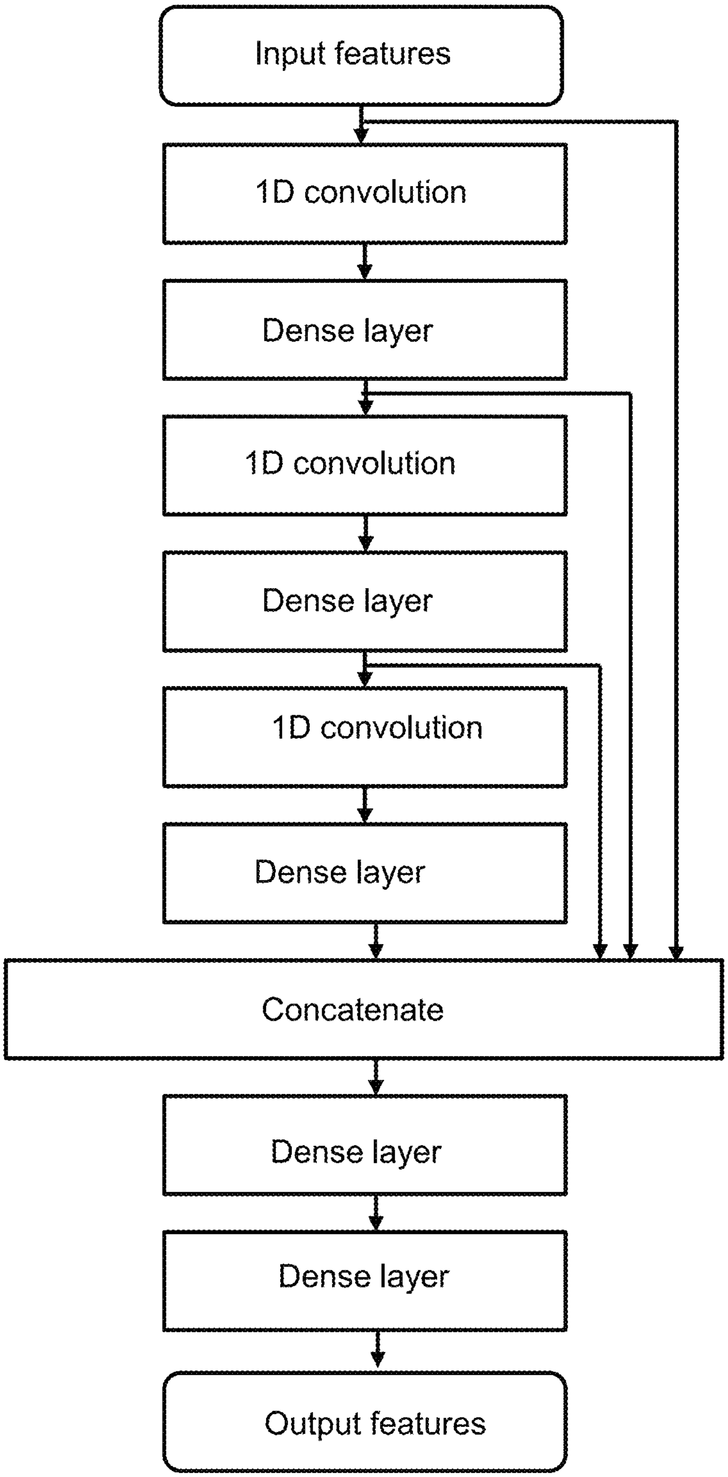
FIG. 4 shows the architecture of the residual blocks of FIG. 3.

FIG. 4 shows the architecture of the residual blocks of FIG. 3.

In an example, re-training the machine learning model shown in FIG. 3 may comprise varying the weights for the first layer 301, third layer 303 and fourth layer 304 while keeping the weight for all other layers (i.e., all other dense layers, convolutional layers, GRUs, including the second layer 302) fixed.

The example re-training process described with respect to FIG. 3 was conducted for 41 subjects. The first re-trained machine learning model was generated during a first night and evaluated using data obtained on a second (consecutive) night. The performance of the first re-trained model was compared to the results obtained using the original trained machine learning model (without re-training) based on the same data obtained during the second night. The performances of both models were compared to recordings of a PSG during the second night. The results are provided in Table 1 and Table 2.

TABLE 1

Performance on the second night using the trained model

| Baseline, N2 | Kappa (—) | Accuracy (%) | Sensitivity (%) | Specificity (%) | PPV |
|---|---|---|---|---|---|
| Wake/N1-N2/N3/REM | 0.62 (0.10) | 75.5 (7.1) | | | |
| Wake/NREM/REM | 0.72 (0.09) | 87.7 (4.2) | | | |
| N1-N2 | 0.53 (0.13) | 76.3 (7.0) | 88.1 (5.7) | 66.5 (9.8) | 69.1 (12.1) |
| N3 | 0.58 (0.17) | 87.5 (5.7) | 54.0 (19.8) | 98.2 (1.8) | 88.2 (11.8) |
| REM | 0.72 (0.13) | 91.9 (4.1) | 70.1 (15.4) | 97.5 (2.7) | 88.3 (10.2) |
| Wake (vs. Sleep) | 0.70 (0.15) | 95.3 (2.1) | 80.5 (16.0) | 96.7 (2.3) | 69.6 (18.5) |

TABLE 1

Performance on the second night using the first re-trained model

| Adapted model, N2 | Kappa (—) | Accuracy (%) | Sensitivity (%) | Specificity (%) | PPV |
|---|---|---|---|---|---|
| Wake/N1-N2/N3/REM | 0.67 (0.08) | 79.0 (5.6) | | | |
| Wake/NREM/REM | 0.76 (0.08) | 89.4 (3.6) | | | |
| N1-N2 | 0.59 (0.10) | 79.9 (5.1) | 86.0 (6.2) | 74.5 (8.3) | 74.0 (10.5) |
| N3 | 0.66 (0.13) | 89.3 (3.8) | 66.7 (16.6) | 96.2 (3.0) | 83.1 (12.6) |
| REM | 0.77 (0.10) | 93.1 (3.5) | 77.0 (11.2) | 97.3 (2.9) | 88.0 (10.8) |
| Wake (vs. Sleep) | 0.70 (0.16) | 95.6 (2.6) | 74.0 (17.8) | 97.5 (2.2) | 74.9 (18.5) |

The neural network also comprises a recurrent neural network (RNN) block 315 comprising a plurality of RNN units. In this example the RNN units are gated recurrent units, GRUs. However, long-short term memory units, LSTMs, could also be used. The RNNs leverage the temporally structured nature of sleep to map the features extracted by the feature extraction block 313 to the output sleep stages while taking into account recent and neighboring feature values. Bidirectional RNNs leverage information from the past (previous epochs, possibly from the beginning of the night up to the current epoch), as well as from the "future" (from the current epoch, until the end of the night). Accordingly, this implementation is non-causal, i.e., the input instant HR and activity counts have to be available for the full night before sleep stage inference is performed. For Table 1 and Table 2 report Cohen's kappa coefficient of agreement for various sleep stages identified in the experience. On average, there is a substantial increase in average four-class sleep stage classification performance, from a kappa of 0.62 to 0.67. Note a particularly large improvement in kappa for REM sleep (from 0.72 to 0.77), and especially for N3 (from 0.58 to 0.66). N3 is known to be one of the most difficult sleep stages to detect using surrogate cardiorespiratory methods. The data shows that overall performance tends to increase using the first re-trained model. Additionally, the between subject variability decreases when a re-trained model is used, suggesting that the subject-specific influences on the performance of the classifier are greatly reduced.

Figure 5:
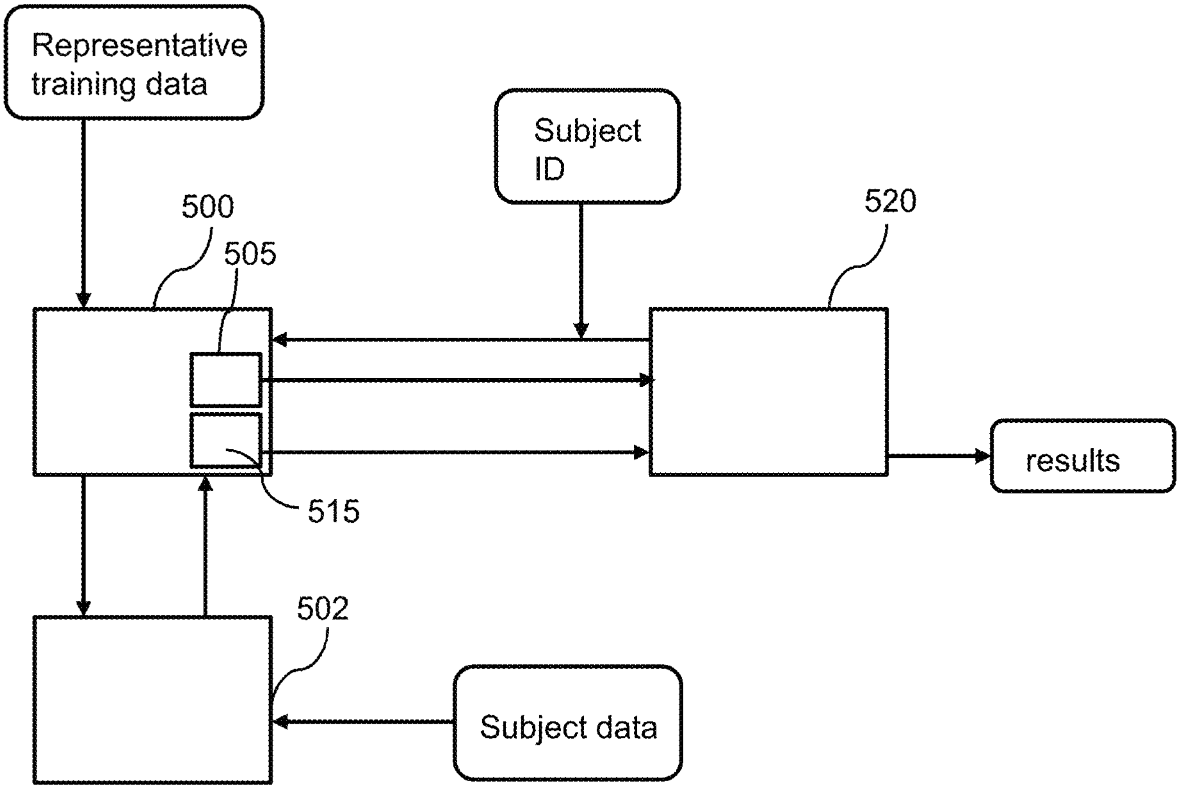
FIG. 5 shows an embodiment of a system for monitoring a physiological status of a subject.

FIG. 5 shows an embodiment of a system for monitoring a physiological status of a subject.

The system 510 comprises a training computer 500 and a database 502. The training computer 500 is configured to generate a trained machine learning model 505 for monitoring a physiological status of a subject. The trained machine learning model 505 is configured to receive, as input, physiological sensor data and determine, as output, a physiological status of the subject, wherein the trained machine learning model is configured to determine the output physiological status of the subject, based on the input physiological sensor data. The training computer 500 is configured to output the trained machine learning model 505. The trained machine learning model can be run by a physiological monitoring system 520.

The training computer 500 is further configured to re-train the machine learning model 505 based on subject data to generate a personalized trained machine learning model 515 (i.e., a trained machine learning model that is personalized to the subject). For example, in response to receiving a request for a trained machine learning model for monitoring a physiological status from the physiological monitoring system 520, the request comprising a subject ID, the training computer 500 uses the subject ID to retrieve relevant subject data from the database 502 and generates a re-trained machine learning model using the subject data.

The re-training of the machine learning model can be performed using data obtained during a dedicated data collection (e.g., a PSG sleep study or HST) together with data obtained using a sensor that will be used to acquire input data in regular use (or an equivalent sensor). The data collected from the subject is associated with a unique identifier: a subject ID. When re-training the machine learning model 505, the training computer 500 retrieves subject data stored in the database 502 by retrieving data associated with the subject ID.

The system outputs the re-trained machine learning model 515 to the physiological monitoring system 520.

The subject data may be obtained by carrying out a PSG sleep study on the subject, which involves obtaining multiple types of data, which data may be relevant to various types of physiological status monitoring. Accordingly, in some embodiments, the training computer 500 is configured to generate multiple trained machine learning models, each for monitoring a different physiological state. In response to a request for a personalized trained machine learning model, received from the physiological monitoring system 520, the training computer 500 outputs a re-trained machine learning model 515. The request comprises both the subject ID and an indication of the sensor data used by the physiological monitoring system 520. Based on this information, the training computer 500 outputs an appropriate re-trained machine learning model 515. For example, the re-trained machine learning model 515 may be configured to: (i) monitor sleep stages based on cardiorespiratory signals, (ii) monitor sleep stages for subjects using positive airway pressure devices, (iii) monitor sleep disordered breathing events, and (iv) monitor sleep stages based on cardiac data and body movement data.

Deployment of the re-trained machine learning model could be carried out in various ways. The model may be carried out via a cloud computation of the measurements of interest, by changing the firmware of the physiological monitoring system, or by configuring the model and classifier on the physiological monitoring system.

Figure 6:
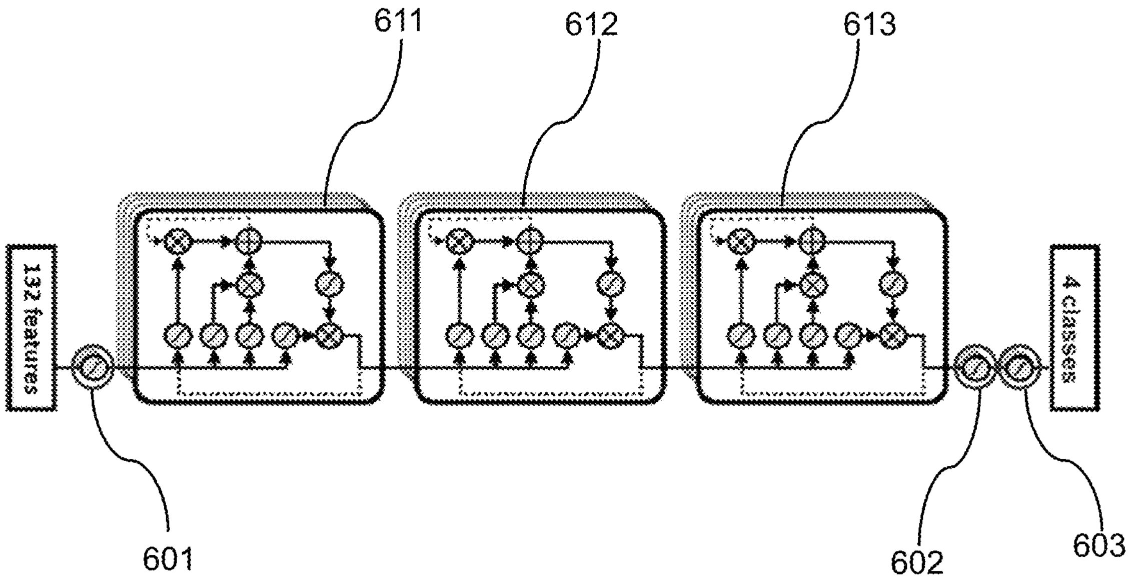
FIG. 6 shows a schematic diagram illustrating the architecture of a trained machine learning model, according to one or more embodiments of the invention.

FIG. 6 shows a schematic diagram illustrating the architecture of a trained machine learning model, according to one or more embodiments of the invention. The model is a neural network in which, manually engineered classifiers are used to determine physiological status. The neural network comprises a first dense layer 601, a second dense layer 602 and a third dense layer 603. It further comprises a first Long Short Term Memory (LSTM) cell 611, a second LSTM cell 612, and a third LSTM cell 613. The dotted black lines denote recurrent connections that pass computed values to the next epoch in the sequence. The sigmoid-like functions are a linear combination of all inputs. Re-training can be carried out by varying the weights associated with one or two of the three dense layers.

In an example, the neural network is configured to monitor sleep stages based on heart rate variability data (e.g., data computed from a sensor capable of measuring measures of inter-beat intervals, such as ECG, finger- or wrist-worn PPG, or an SCG from an accelerometer mounted on the chest).

The manually engineered classifiers may comprise time domain features such as means and medians of HR and RR (detrended and absolute) SDNN, RR range, pNN50, RMSSD, and SDSD, MAD (both detrended and absolute RR), Percentiles (5%, 10%, 25%, 50%, 75%, 90% and 95%) of detrended and absolute HR/RR, RR DFA, its short, long exponents and all scales, and WDFA over 330 s and PDFA over non-overlapping segments of 64 heartbeats, frequency domain features such as RR logarithmic VLF, LF, and HF power and LF-to-HF ratio on 270 s windows, Boundary-adapted RR logarithmic VLF, LF, and HF power and LF-to-HF ratio on 270 s windows, RR mean respiratory frequency and power, max phase and module in HF pole, entropy and regularity features such as Multiscale sample entropy 1 of RR intervals at length 1 and 2, scales 1-10 over 510 s, sample entropy of symbolic binary changes in RR intervals, short- and long-range phase coordination of R-R intervals in patterns of up to 8 consecutive heartbeats, phase synchronization for 6:2, 7:2, 8:2 and 9:2 phases, dominant ratio, short- and long-term coordination, Higuchi's fractal dimension of the normalized IBI sequence and/or other features such as mean teager energy, % of transition points and maxima and mean and standard deviation (SD) of intervals between them, mean and standard deviation of the amplitude of normalized IBIs at transition points and maxima, arousal probabilities (max, mean, median, min, SD), visibility graph features (where HR heart rate; RR R-R interval; SDNN standard deviation of RR; pNN50 percentage of successive RR differences >50 ms; RMSSD, root mean square of successive RR differences; SDSD, standard deviation of successive RR differences; MAD, mean absolute difference; VLF, very low frequency; LF, low frequency; HF, high frequency; DFA, detrended fluctuation analysis; PDFA, progressive DFA; WDFA, windowed DFA; PSD, power spectral density).

Figure 7:
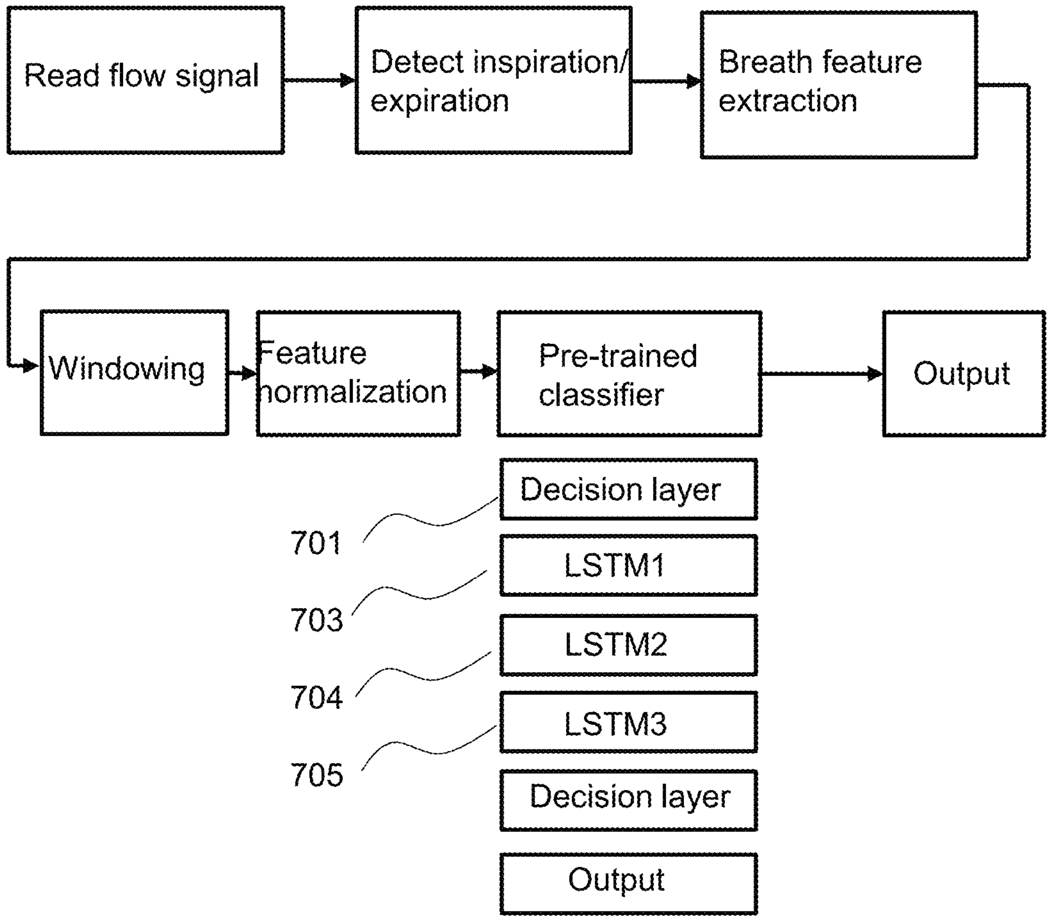
FIG. 7 shows another example architecture of a machine learning model according to one or more embodiments.

FIG. 7 shows another example architecture of a machine learning model according to one or more embodiments.

Monitoring of sleep stages can be carried out using a sleep stage classifier based on respiratory parameters, such as airflow. In FIG. 7, the classifier makes use of engineered features to describe different characteristics of individual breaths based on the airflow (and optionally pressure) sensor data. For example, data is obtained from a sensor integrated in a continuous positive airway pressure device.

The airflow data is analyzed to detect inspiration and/or expiration and to extract breath features. These features are further processed with statistical windowing methods, and after normalization, used as input to a classifier. The classifier determines sleep stage (e.g., awake, N1+N2, N3 or REM) based on the input features, and outputs the determined sleep stage.

As shown in FIG. 7, the classifier comprises an initial decision layer 701, a first LSTM layer 703, a second LSTM layer 704 and a third LSTM layer 705. It further comprises a final decision layer and an output layer. The initial decision layer, final decision layer and output layer are all dense layers.

The neural network can be re-trained, for example, by changing the weights of one or more of the initial decision layer, final decision layer and output layer. This ensures that the classifier would retain the long-term knowledge of the LSTMs trained with the larger training sets, while adjusting to the slightly different feature characteristics of the individual subject.

In some embodiments, the machine learning model is configured to detect sleep disordered breathing events (such as apneas or hypopneas). The machine learning model could be for an example an end-to-end deep neural network. Model adaptation could follow a similar strategy as described above for the end-to-end deep neural network sleep stage classifier.

Figure 8:
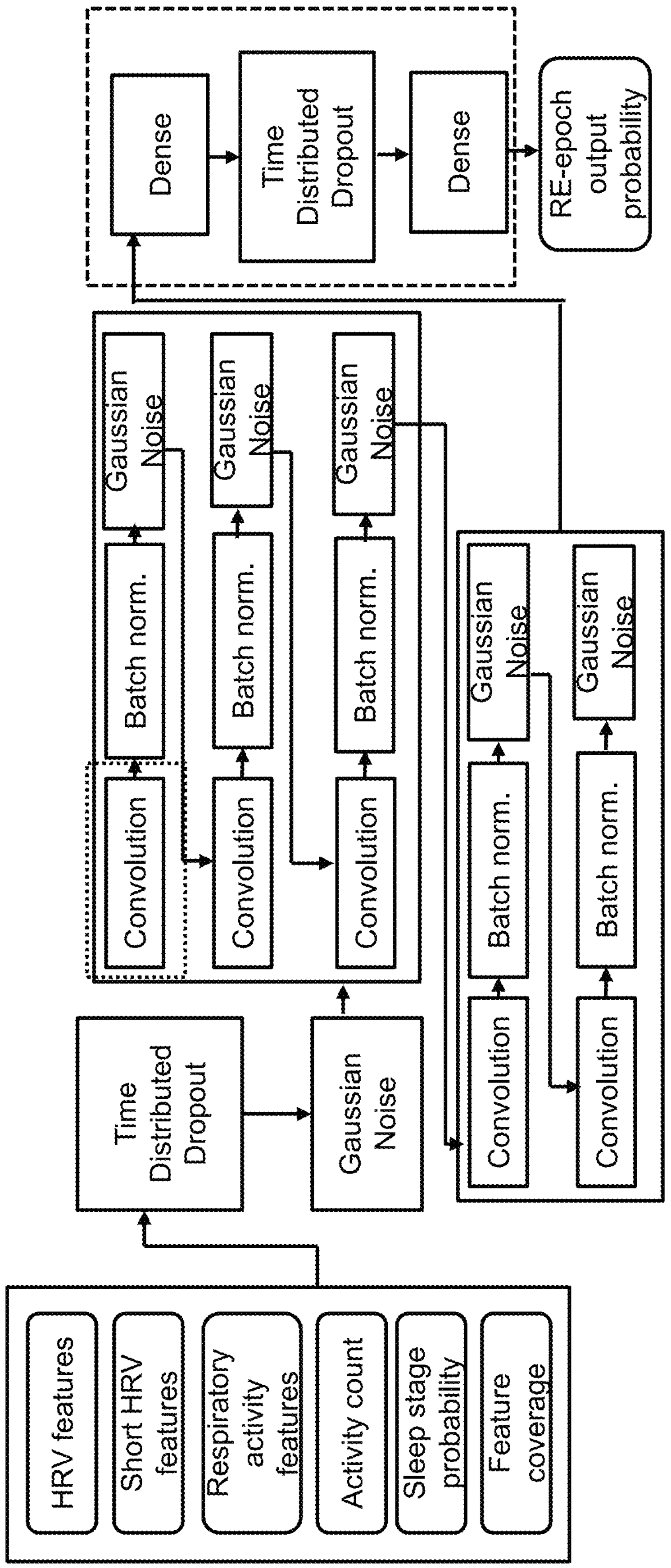
FIG. 8 shows another example architecture of a machine learning model according to one or more embodiments.

FIG. 8 shows another example architecture of a machine learning model according to one or more embodiments. In this model, a feature-based classifier is used. The classifier and makes use of a combination of HRV features, respiratory activity features, activity counts, and even the estimation of sleep stages, all extracted from wrist-worn PPG (or comparable sensor) and accelerometer. In this example, re-training of the machine learning model could be performed by re-training only one or more of the neural network layers surrounded by a dashed rectangle.

Figure 9:
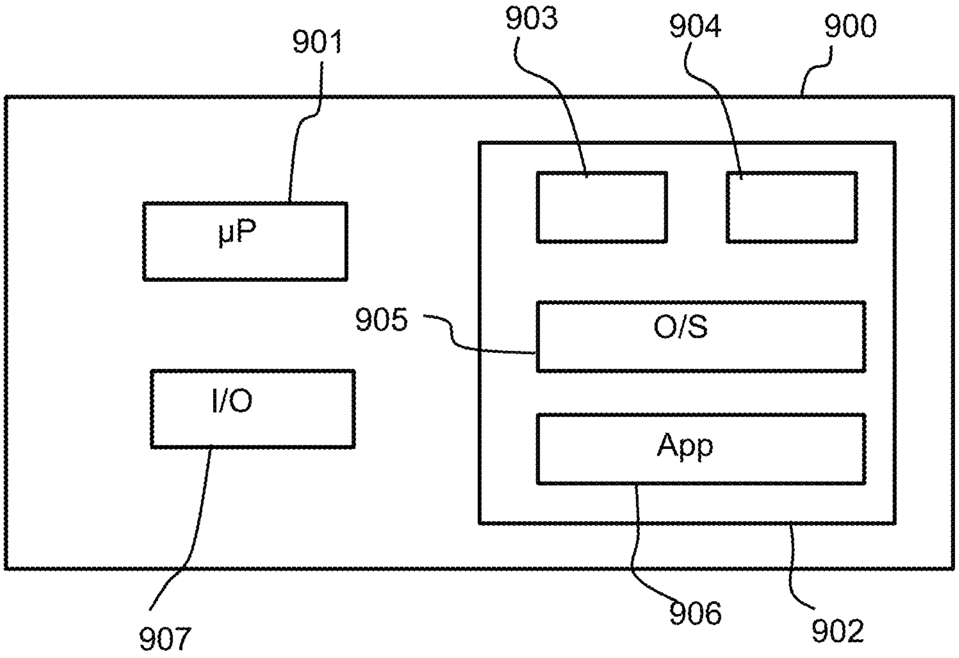
FIG. 9 shows a computer for carrying out one or more of the methods disclosed herein.

FIG. 9 is a schematic diagram of a computer for carrying out one or more of the methods disclosed herein.

FIG. 9 illustrates an example of a computer 900 within which one or more parts of an embodiment may be employed. Various operations discussed above may utilize the capabilities of the computer 900. For example, one or more parts of a system for processing an image with a CNN may be incorporated in any element, module, application, and/or component discussed herein. In this regard, it is to be understood that system functional blocks can run on a single computer or may be distributed over several computers and locations (e.g., connected via internet).

The computer 900 includes, but is not limited to, PCs, workstations, laptops, PDAs, palm devices, servers, storages, and the like. Generally, in terms of hardware architecture, the computer 900 may include one or more processors 901, memory 902, and one or more I/O devices 907 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 901 is a hardware device for executing software that can be stored in the memory 902. The processor 901 can be virtually any custom made or commercially available processor, a central processing unit (CPU), a digital signal processor (DSP), or an auxiliary processor among several processors associated with the computer 900, and the processor 901 may be a semiconductor-based microprocessor (in the form of a microchip) or a microprocessor.

The memory 902 can include any one or combination of volatile memory elements (e.g., random access memory (RAM), such as dynamic random access memory (DRAM), static random access memory (SRAM), etc.) and non-volatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 902 may incorporate electronic, magnetic, optical, and/or other types of storage media. Note that the memory 902 can have a distributed architecture, where various components are situated remote from one another, but can be accessed by the processor 901.

The software in the memory 902 may include one or more separate programs, each of which comprises an ordered listing of executable instructions for implementing logical functions. The software in the memory 902 includes a suitable operating system (O/S) 905, compiler 904, source code 903, and one or more applications 906 in accordance with exemplary embodiments. As illustrated, the application 906 comprises numerous functional components for implementing the features and operations of the exemplary embodiments. The application 906 of the computer 900 may represent various applications, computational units, logic, functional units, processes, operations, virtual entities, and/or modules in accordance with exemplary embodiments, but the application 906 is not meant to be a limitation.

The operating system 905 controls the execution of other computer programs, and provides scheduling, input-output control, file and data management, memory management, and communication control and related services. It is contemplated by the inventors that the application 906 for implementing exemplary embodiments may be applicable on all commercially available operating systems.

Application 906 may be a source program, executable program (object code), script, or any other entity comprising a set of instructions to be performed. When a source program, then the program is usually translated via a compiler (such as the compiler 904), assembler, interpreter, or the like, which may or may not be included within the memory 902, so as to operate properly in connection with the O/S 905. Furthermore, the application 906 can be written as an object oriented programming language, which has classes of data and methods, or a procedure programming language, which has routines, subroutines, and/or functions, for example but not limited to, C, C++, C #, Pascal, BASIC, API calls, HTML, XHTML, XML, ASP scripts, JavaScript, FORTRAN, COBOL, Perl, Java, ADA, .NET, and the like.

The I/O devices 907 may include input devices such as, for example but not limited to, a mouse, keyboard, scanner, microphone, camera, etc. Furthermore, the I/O devices 907 may also include output devices, for example but not limited to a printer, display, etc. Finally, the I/O devices 907 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 907 also include components for communicating over various networks, such as the Internet or intranet.

If the computer 900 is a PC, workstation, intelligent device or the like, the software in the memory 902 may further include a basic input output system (BIOS) (omitted for simplicity). The BIOS is a set of essential software routines that initialize and test hardware at startup, start the O/S 905, and support the transfer of data among the hardware devices. The BIOS is stored in some type of read-only-memory, such as ROM, PROM, EPROM, EEPROM or the like, so that the BIOS can be executed when the computer 900 is activated.

When the computer 900 is in operation, the processor 901 is configured to execute software stored within the memory 902, to communicate data to and from the memory 902, and to generally control operations of the computer 900 pursuant to the software. The application 906 and the O/S 905 are read, in whole or in part, by the processor 901, perhaps buffered within the processor 901, and then executed.

When the application 906 is implemented in software it should be noted that the application 906 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

The application 906 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium.

In an embodiment of the invention, there is provided a computer implemented method of providing physiological status monitoring. The method comprises receiving subject data, the subject data comprising physiological sensor data and reference physiological status data; and adapting a trained machine learning model for monitoring a physiological status. The trained machine learning model is configured to receive, as input, physiological sensor data and determine, as output, a physiological status of the subject. The trained machine learning model is configured to determine the output physiological status of the subject, based on the input physiological data, according to a plurality of weights. Adapting the trained machine learning model comprises: re-training the trained machine learning model, based on the subject data by: maintaining the values of a fixed set of the plurality of weights; and changing the values of a variable set of the plurality of weights. For example, the machine learning is a trained neural network.

For example, the physiological sensor data indicates a physiological parameter indicative of a physiological status, and the reference physiological status data indicates a physiological status correlated with the physiological parameter.

The trained machine learning model may be configured to provide sleep monitoring, the physiological sensor data comprises autonomic nervous system activity data, and the physiological status is a sleep stage, a sleep disordered breathing event or an arousal event. For example, the physiological sensor data comprises accelerometer data, cardiac data and/or respiratory data.

The physiological sensor data comprises, for example, neurological activity data and/or central nervous system activity data.

The physiological sensor data comprises, for example, cardiac data and the physiological condition is a cardiac-related condition.

For example, the method comprises further obtaining subject data by: obtaining, over a re-training period, representative physiological sensor data, wherein the representative physiological sensor data comprises autonomic nervous system activity data; and obtaining reference physiological status data, wherein the reference physiological status data indicates a ground truth associated with the monitored physiological status during the re-training period.

For example, the method further comprises generating the trained machine learning model by: obtaining physiological sensor training data for a plurality of participants; obtaining reference training information, wherein the reference training information indicates a ground-truth associated with monitored physiological status; and inputting the physiological sensor training data and the reference training information into to the machine learning model.

For example, the method further comprises obtaining a plurality of subject data sets, each data set corresponding to a respective time period; and determining the number of fixed weights based on the number of subject data sets.

For example, the method comprises obtaining a plurality of subject data sets, each data set corresponding to a respective time period, the method further comprising: generating a first re-trained machine learning model by adapting the trained machine learning model based on a first subject data set corresponding to a first time period; generating a second re-trained machine learning model by adapting the trained machine learning model based on the first subject data set and a second subject data set, the second subject data set corresponding to a second time period; and evaluating the performance of the first re-trained machine learning model and the second re-trained machine learning model; and in response to determining that the performance of the first re-trained machine learning model is superior to the second re-trained machine learning model, preventing re-training of the machine learning model from using the second subject data set. Optionally, the evaluating the performance of the first trained machine learning model and the second trained machine learning model comprises: for each of the first machine learning model network and the second trained machine learning model, determining the degree of agreement between the output of the trained machine learning model and the adapted machine learning model.

In an embodiment, there is provided a system for monitoring a physiological status, the system comprising a processor configured to carry out the steps of any of the embodiments mentioned above. Optionally, the system further comprises: a database storing the trained machine learning model and the subject data, wherein the processor is configured to retrieve the trained machine learning model and the subject data from the database and/or a physiological sensor for obtaining the physiological sensor data, and optionally wherein the physiological sensor is configured to measure an autonomic nervous system parameter.

In an embodiment, there is provided a computer program product comprising computer program code means which, when executed on a computing device having a processor, cause the processor to perform all of the steps of the method according to any of the embodiments above.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

Functions implemented by a processor may be implemented by a single processor or by multiple separate processing units which may together be considered to constitute a "processor". Such processing units may in some cases be remote from each other and communicate with each other in a wired or wireless manner.

The mere fact that certain measures are recited in mutually different dependent claims does not indicate that a combination of these measures cannot be used to advantage.

A computer program may be stored/distributed on a suitable medium, such as an optical storage medium or a solid-status medium supplied together with or as part of other hardware, but may also be distributed in other forms, such as via the Internet or other wired or wireless telecommunication systems.

If the term "adapted to" is used in the claims or description, it is noted the term "adapted to" is intended to be equivalent to the term "configured to". If the term "arrangement" is used in the claims or description, it is noted the term "arrangement" is intended to be equivalent to the term "system", and vice versa.

Any reference signs in the claims should not be construed as limiting the scope.

It will be appreciated that various types of physiological status monitoring can be carried out according to embodiments of the invention. In some embodiments, the physiological status is sleep-related and the physiological sensor data comprise cardiorespiratory data. For example, the physiological sensor data may comprise instantaneous heart rate data and/or heart rate variability data. The data may be obtained by a PPG sensor. The physiological sensor data may comprise body movement data e.g., obtained by an accelerometer.

The physiological status may not be sleep related. For example, physiological status may indicate the presence or absence of a physiological condition such as atrial fibrillation, high blood pressure or low blood pressure.

In some embodiments, the machine learning model uses a plurality of manually engineered classifiers for determining physiological state based on physiological sensor data.

It will be appreciated that the specific machine learning model architectures discussed above (e.g., in connection with FIGS. 3, 6, 7 and 8) are example architectures. The skilled person will appreciate that other architectures are available.

The invention claimed is:

1. A computer-implemented method for providing physiological status monitoring, the method comprising:

receiving subject data comprising physiological sensor data of a subject;

and adapting a trained machine learning model for monitoring a physiological status, wherein the trained machine learning model is configured to determine the physiological status of the subject based on the physiological sensor data, wherein the trained machine learning model has a plurality of fixed weights and a plurality of variable weights;

wherein adapting the trained machine learning model comprises: generating a first re-trained machine learning model by adapting the trained machine learning model by maintaining values of the plurality of fixed weights, and changing values of a first number of the plurality of variable weights;

determining a level of agreement between the trained machine learning model and the first re-trained machine learning model, wherein the level of agreement is indicative of a difference between the values of the first number of the plurality of variable weights of the trained machine learning model and the values of the first number of the first re-trained machine learning model;

based on the level of agreement, generating a second re-trained machine learning model by adapting the trained machine learning model by maintaining the values of the plurality of fixed weights, and changing values of a second number of the plurality of variable weights, wherein the second number is different from the first number and is smaller than the first number when the level of agreement satisfies a threshold condition indicating overfitting.

2. The method of claim 1, wherein the level of agreement is indicative of a difference of a performance of the trained machine learning model and a performance of the first re-trained machine learning model.

3. The method of claim 1, wherein the trained machine learning model is a trained neural network.

4. The method of claim 1, wherein the physiological sensor data indicates a physiological parameter indicative of a physiological status, and the subject data comprises reference physiological status data indicating a physiological status correlated with the physiological parameter.

5. The method of claim 1, wherein the trained machine learning model is configured to provide sleep monitoring, the physiological sensor data comprises autonomic nervous system activity data, and the physiological status is a sleep stage, a sleep disordered breathing event or an arousal event.

6. The method of claim 5, wherein the physiological sensor data comprises accelerometer data, cardiac data and/or respiratory data.

7. The method of claim 1, wherein the physiological sensor data comprises neurological activity data and/or central nervous system activity data.

8. The method of claim 1, wherein the physiological sensor data comprises cardiac data and the physiological status is a cardiac-related condition.

9. The method of claim 1, further comprising generating the trained machine learning model by:

obtaining physiological sensor training data for a plurality of participants;

obtaining reference training information, wherein the reference training information indicates a ground-truth associated with monitored physiological status;

and inputting the physiological sensor training data and the reference training information into the machine learning model.

10. The method of claim 1, further comprising:

obtaining a plurality of subject data sets, each data set corresponding to a respective time period;

and determining the number of fixed weights based on the number of subject data sets.

11. The method of claim 1, wherein the method comprises obtaining a plurality of subject data sets, each data set corresponding to a respective time period, the method further comprising:

generating the first re-trained machine learning model by adapting the trained machine learning model based on a first subject data set corresponding to a first time period;

generating the second re-trained machine learning model by adapting the trained machine learning model based on the first subject data set and a second subject data set, the second subject data set corresponding to a second time period;

and evaluating the performance of the first re-trained machine learning model and the second re-trained machine learning model;

and in response to determining that the performance of the first re-trained machine learning model is superior to the second re-trained machine learning model, preventing re-training of the machine learning model from using the second subject data set.

12. A system for monitoring a physiological status, the system comprising:

a processor configured to carry out the steps of claim 1.

13. A non-transitory computer readable medium comprising computer program code instructions which, when executed on a computing device having a processor, cause the processor to perform all of the steps of the method according to claim 1.

* * * * *